US010848612B2

(12) United States Patent
Sheng et al.

(10) Patent No.: US 10,848,612 B2
(45) Date of Patent: Nov. 24, 2020

(54) SYSTEM AND METHOD FOR MOBILE DEVICE TO AUTOMATICALLY DISABLE FINGERPRING UNLOCK WHEN USER IS SLEEPING (71) Applicant: ARRIS Enterprises LLC, Suwanee, GA (US)

(72) Inventors: Libo Sheng, Shanghai (CN); Jianguo Zhou, Shanghai (CN); Fenggen Hu, Shanghai (CN)

(73) Assignee: ARRIS Enterprises LLC, Suwanee, GA (US)

( * ) Notice: Subject to any disclaimer, the term of this patent is extended or adjusted under 35 U.S.C. 154(b) by 0 days.

(21) Appl. No.: 15/551,502

(22) PCT Filed: Dec. 19, 2016

(86) PCT No.: PCT/CN2016/110856
§ 371 (c)(1),
(2) Date: Aug. 16, 2017

(87) PCT Pub. No.: WO2018/112713
PCT Pub. Date: Jun. 28, 2018

(65) Prior Publication Data
US 2019/0312967 A1    Oct. 10, 2019

(51) Int. Cl.
*H04M 1/72*    (2006.01)
*H04M 1/725*    (2006.01)
(Continued)

(52) U.S. Cl.
CPC ....... *H04M 1/72577* (2013.01); *A61B 5/4809* (2013.01); *G06F 21/32* (2013.01);
(Continued)

(58) Field of Classification Search
CPC .... A61B 5/6898; G06F 1/163; G08B 21/0453
(Continued)

(56) References Cited

U.S. PATENT DOCUMENTS 10,653,856 B2 *    5/2020    Freed .................. A61B 5/6898
2005/0281531 A1    12/2005    Unmehopa
(Continued)

FOREIGN PATENT DOCUMENTS

| CN | 105611531 A | 5/2016 |
| CN | 105678133 A | 6/2016 |
| CN | 105975828 A | 9/2016 |

OTHER PUBLICATIONS

PCT International Search Report & Written Opinion, Re: Application No. PCT/CN2016/110856, dated Sep. 6, 2017.

*Primary Examiner* — Kiet M Doan
(74) *Attorney, Agent, or Firm* — Wenderoth, Lind & Ponack, L.L.P.

(57) ABSTRACT

A device includes a processing component, a user interface component, a locking component, a biometric parameter unlock component, a detecting component and a sleep bypass component. The processing component performs a processing function. The user interface component instructs the processing component to perform the processing function. The locking component prevents the user interface component from instructing the processing component to perform the processing function. The biometric parameter unlock component detects a biometric parameter of the user and disables the locking component to enable the user interface component to instruct the processing component to perform the processing function. The detecting component generates a sleep signal based on a detected sleeping parameter of the user indicating that the user is asleep. The sleep bypass component disables biometric parameter unlock component based on the sleep signal.

20 Claims, 7 Drawing Sheets (51) Int. Cl.
*A61B 5/00* (2006.01)
*G06F 21/32* (2013.01)
*G06F 21/35* (2013.01)
*G06F 21/84* (2013.01)

(52) U.S. Cl.
CPC ........ *G06F 21/35* (2013.01); *H04M 1/72569* (2013.01); *G06F 21/84* (2013.01)

(58) Field of Classification Search
USPC ............... 455/411, 412.1, 418, 410, 558; 340/573.1, 539.11; 700/282, 91; 434/236
See application file for complete search history.

(56) References Cited

U.S. PATENT DOCUMENTS

| | | | |
|---|---|---|---|
| 2008/0229409 A1* | 9/2008 | Miller | G06F 21/32 726/19 |
| 2016/0073950 A1* | 3/2016 | Franceschetti | H05B 1/0272 340/575 |
| 2016/0119789 A1 | 4/2016 | Hu et al. | |
| 2016/0210407 A1* | 7/2016 | Hwang | G06Q 50/22 |

\* cited by examiner

PRIOR ART

FIG. 1

PRIOR ART

SYSTEM AND METHOD FOR MOBILE DEVICE TO AUTOMATICALLY DISABLE FINGERPRING UNLOCK WHEN USER IS SLEEPING

BACKGROUND

Embodiments of the invention relate to devices and methods to maintain security in an electronic device.

Figure 1:
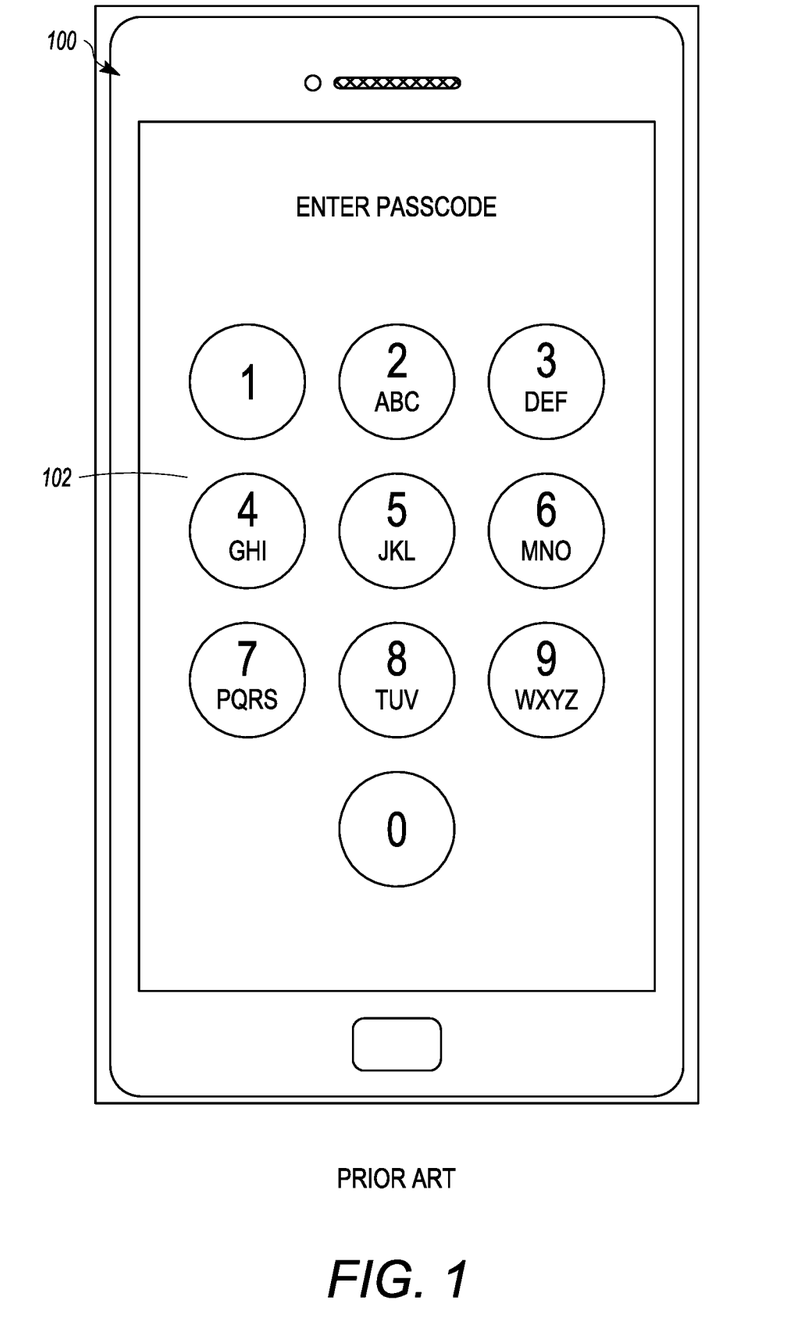
FIG. 1 illustrates a conventional mobile device unlock screen.

FIG. 1 illustrates a conventional mobile device unlock screen.

As shown in the figure, a mobile device 100 includes an unlock screen 102.

Mobile device 100 may be a smartphone, tablet computer, handheld computer, or any other type of device that provides a user the ability to compute and communicate without being tethered by wires.

Unlock screen 102 may include numbers, but it may also include any other type of display that provides a user the ability to unlock mobile device 100.

In operation, when mobile device 100 is locked, a user is unable to engage with mobile device 100 to make phone calls or open applications. To unlock mobile device 100, a user must enter the correct passcode on unlock screen 102. If unlock screen 102 includes numbers, the user must enter the correct combination of numbers to unlock mobile device 100. In some embodiments, unlock screen 102 includes an array of dots the user must connect in a specific pattern to unlock mobile device 100. After entering the correct combination of numbers or connecting the dots in the correct pattern, mobile device 100 is unlocked and the user can engage with mobile device 100 as desired.

Figure 2:
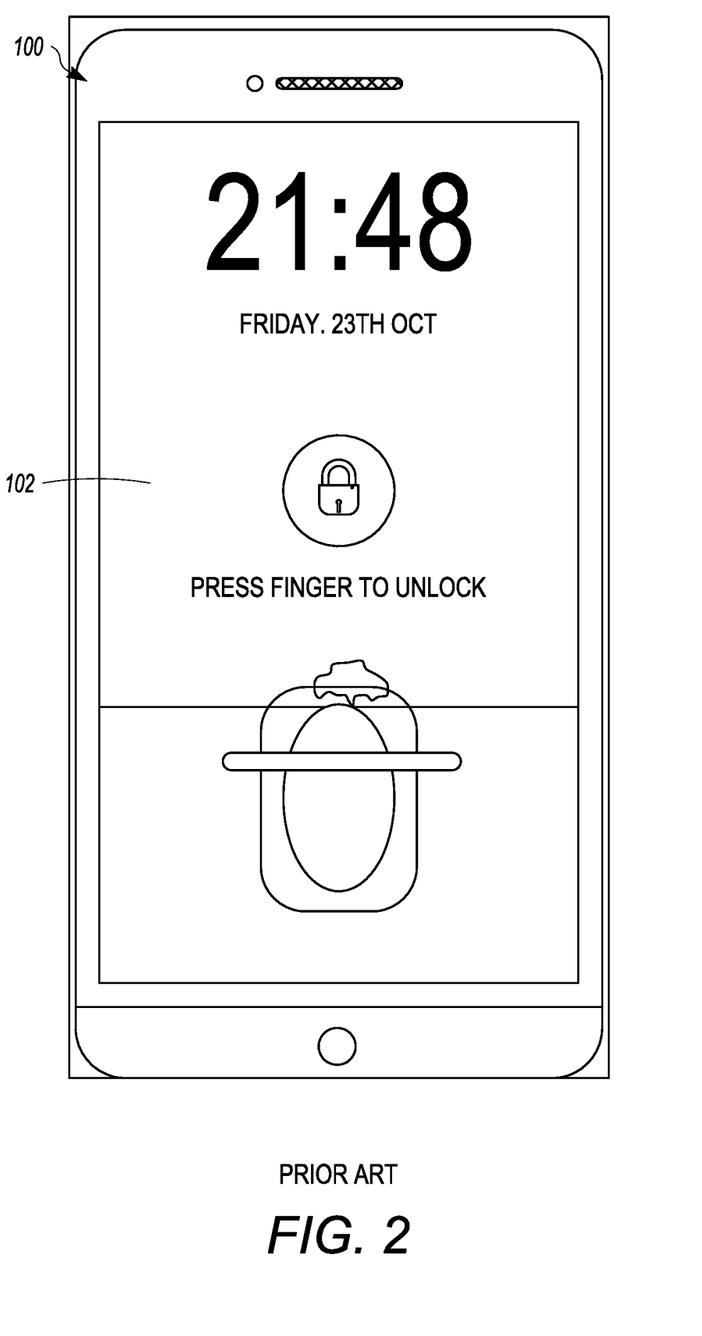
FIG. 2 illustrates another conventional mobile device unlock screen.

FIG. 2 illustrates another conventional mobile device unlock screen.

As shown in the figure, mobile device 100 includes an unlock screen 202.

Unlock screen 202 includes a fingerprint recognition area, where a user places his finger on unlock screen 202. When the user's finger is on the fingerprint recognition area, mobile device 100 scans the user's fingerprint and compares it to a stored image of the user's fingerprint. If the scanned fingerprint matches the stored image, mobile device 100 will unlock. In an alternate embodiment, unlock screen 202 may include face recognition where mobile device 100 scans the user's face and compares the scan to a stored image of the user's face. If the scanned image matches the stored image, mobile device 100 will unlock. In other embodiments, unlock screen 202 may include retina recognition or voice recognition that function in the same way as described above with reference to face and fingerprint recognition.

Though biometric based security previously demonstrated by unlock screen 202 are convenient for users, they can also be problematic. For example, if a user is sleeping, a criminal may fraudulently use the user's biometric data to unlock the user's phone. The criminal may hold the user's finger to the unlock screen to unlock the mobile device, after which the criminal can go in to applications on the user's phone, like the user's bank account, and steal from the user.

There exists a need for additional mobile device security when a user is sleeping or otherwise unconscious.

SUMMARY

Aspects of the present invention are drawn to a device for use by a user, wherein the device includes a processing component, a user interface component, a locking component, a biometric parameter unlock component, a detecting component and a sleep bypass component. The processing component performs a processing function. The user interface component instructs the processing component to perform the processing function. The locking component prevents the user interface component from instructing the processing component to perform the processing function. The biometric parameter unlock component detects a biometric parameter of the user and disables the locking component to enable the user interface component to instruct the processing component to perform the processing function. The detecting component generates a sleep signal based on a detected sleeping parameter of the user indicating that the user is asleep. The sleep bypass component disables biometric parameter unlock component based on the sleep signal.

BRIEF SUMMARY OF THE DRAWINGS

The accompanying drawings, which are incorporated in and form a part of the specification, illustrate example embodiments and, together with the description, serve to explain the principles of the invention. In the drawings.

DETAILED DESCRIPTION

Aspects of the present invention are drawn to a device and method to provide additional mobile device security when a user is sleeping or otherwise unconscious.

Aspects of the present invention prevent unauthorized use of a mobile device by disabling mobile device biometric unlocking features when a user of a mobile device is sleeping or otherwise unconscious. The mobile device receives biometric information from a wearable device the user is wearing, or from direct contact with the user himself. The mobile device uses the biometric information to determine whether the user is sleeping, and if the user is sleeping, the mobile device disables the biometric unlock feature on the mobile device. In this manner, the mobile device will not be unlocked with the biometric unlock feature, thus preventing a person from holding the user's finger to the unlock screen to unlock the mobile device.

Aspects of the present invention will now be described with reference to FIGS. 3-7.

Figure 3:
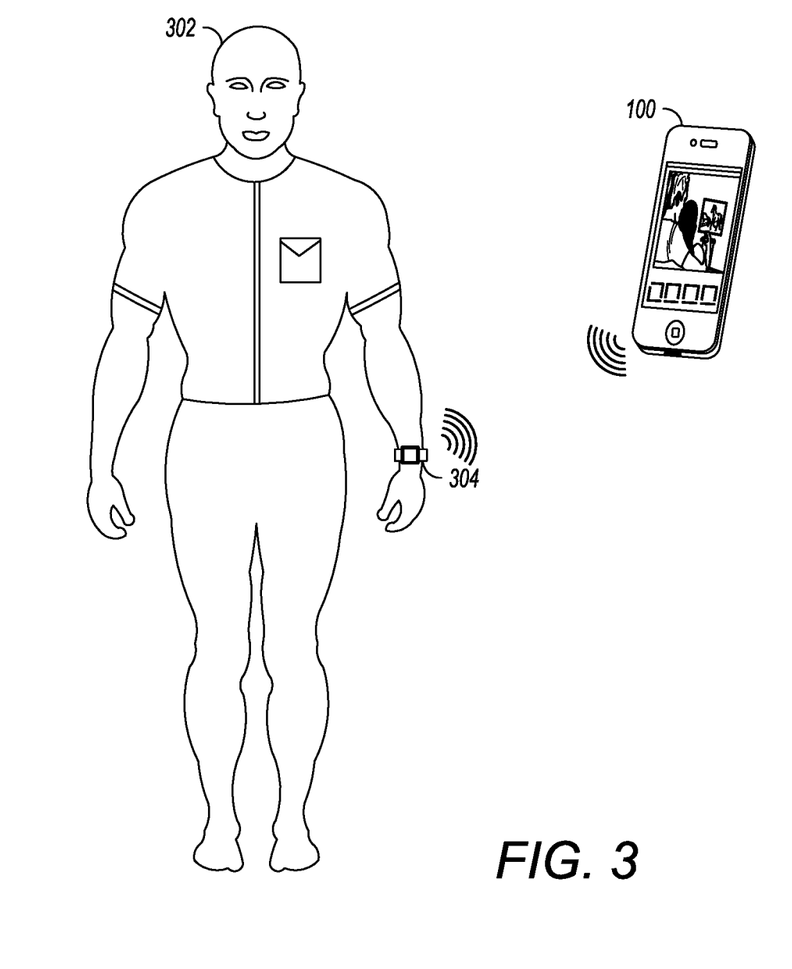
FIG. 3 illustrates communication between a mobile device and a wearable device when a user is awake.

FIG. 3 illustrates communication between a mobile device and a wearable device when a user is awake.

As shown in the figure, user 302 is wearing wearable device 304 and wearable device 304 is in communication with mobile device 100.

Wearable device 304 may be any type of device user 302 can wear that can also track biometric parameters. Non-limiting examples of wearable device 304 include smart watches, smart clothing, smart shoes, smart headbands, and fitness trackers. Non-limiting examples of biometric parameters wearable device 304 can track include heart rate, pulse, blood pressure, respiration, change in pulse, change in heart rate, change in blood pressure, and change in respiration.

In operation, wearable device 304 is paired with mobile device 100 by any conventional pairing means. Once paired, wearable device 304 and mobile device 100 can communicate via any conventional short distance communication means. A non-limiting example of means by which mobile device 100 and wearable device 304 can communicate is Bluetooth.

When user 302 is awake, wearable device tracks the biometric parameters of user 302 and sends them to mobile device 100. As user 302 performs different activities throughout the day, the biometric parameters will change. For example, when user 302 is sitting at his desk at work, his heart rate, respiration, blood pressure, and any changes thereof, may fluctuate as user 302 performs different activities like typing, talking on the phone, or walking to a meeting. After work, user 302 may go to the gym and exercise. During exercise, his heart rate, respiration, blood pressure, and any changes thereof, will vary greatly from when user 302 was working and will change throughout the workout.

Mobile device 100 receives all of the data from wearable device 304 and can provide the data to user 302 when user 302 desires to see the data to track his activity for the date.

Figure 4:
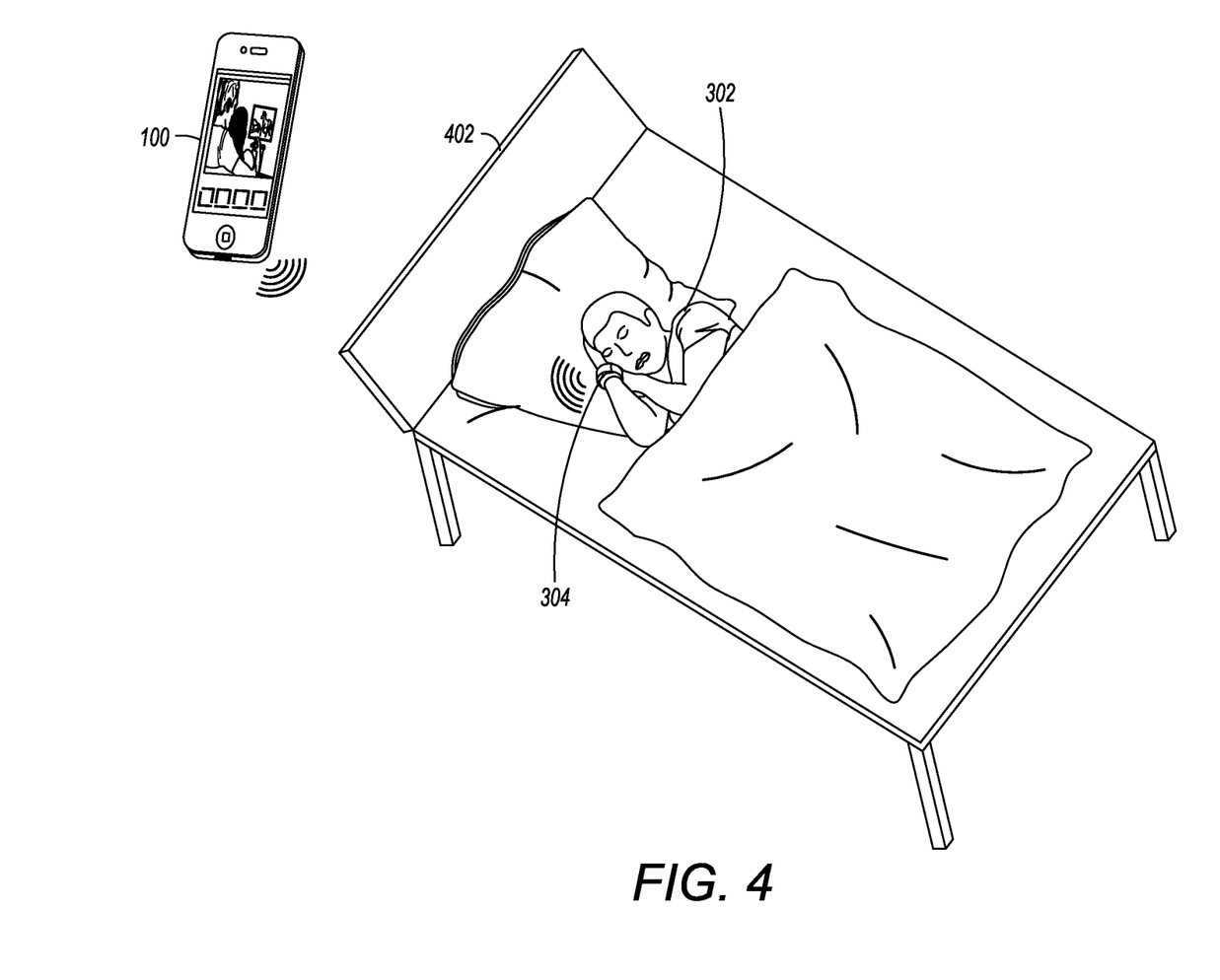
FIG. 4 illustrates communication between a mobile device and a wearable device when a user is asleep.

FIG. 4 illustrates communication between a mobile device and a wearable device when a user is asleep.

As shown in the figure, user 302 is wearing wearable device 304 while sleeping in bed 402. Wearable device 304 is in communication with mobile device 100.

When user 302 is sleeping, wearable device tracks the biometric parameters of user 302 and sends them to mobile device 100. Biometric parameters like pulse, respiration, and blood pressure may be different during sleep than when awake. When mobile device 100 receives the biometric parameters, mobile device 100 can determine whether user 302 is sleeping or awake.

Figure 5:
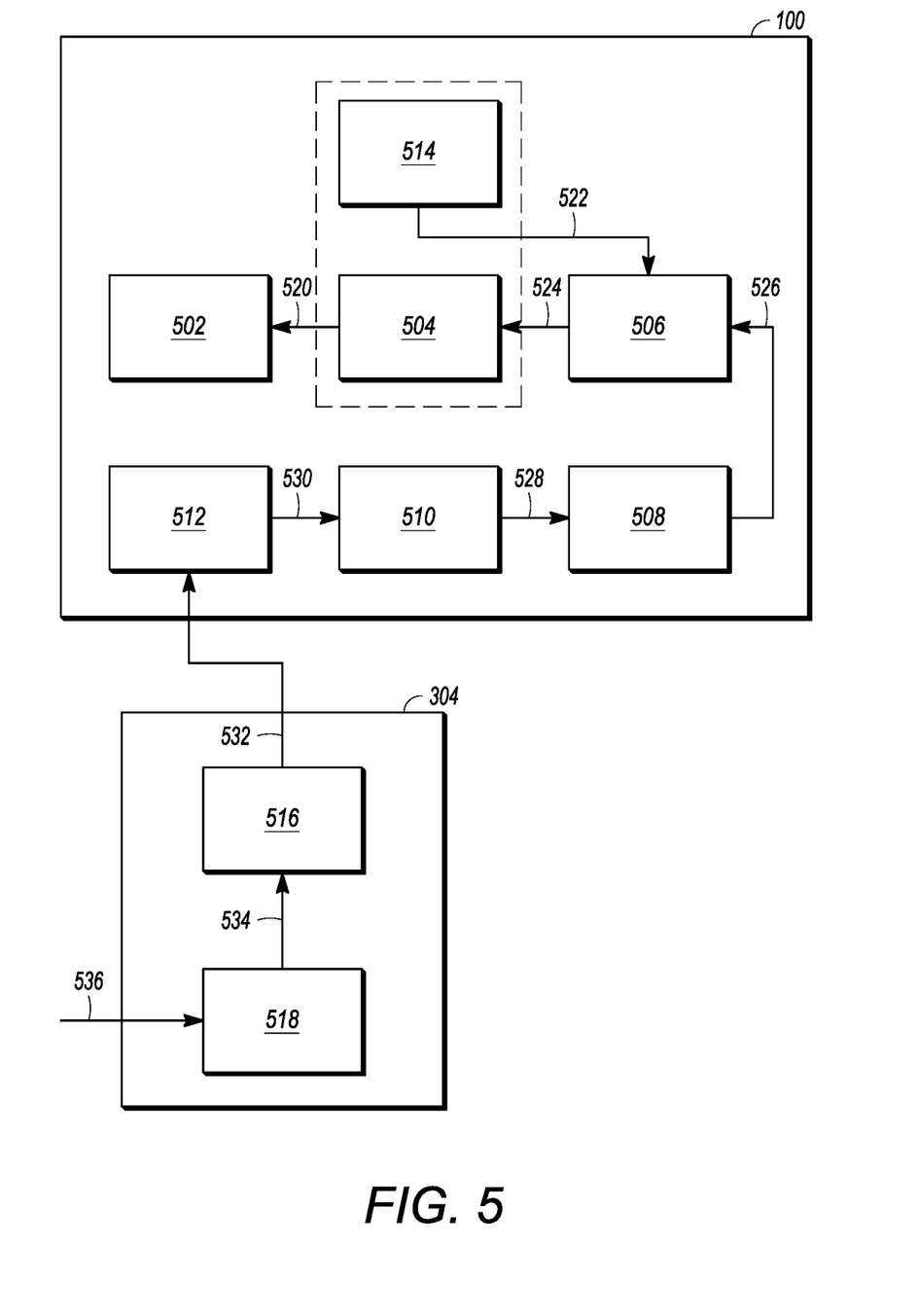
FIG. 5 illustrates a block diagram of a mobile device and a wearable device in accordance with aspects of the present invention.

FIG. 5 illustrates a block diagram of a mobile device and a wearable device in accordance with aspects of the present invention.

As shown in the figure, mobile device 100 includes processing component 502, user interface component 504, locking component 506, biometric parameter unlock component 508, sleep bypass component 510, communication component 512, and unlock component 514. Wearable device 304 includes communication component 516 and detecting component 518.

In this example, processing component 502, user interface component 504, locking component 506, biometric parameter unlock component 508, sleep bypass component 510, communication component 512, and unlock component 514 are illustrated as individual devices. However, in some embodiments, at least two of processing component 502, user interface component 504, locking component 506, biometric parameter unlock component 508, sleep bypass component 510, communication component 512, and unlock component 514 may be combined as a unitary device.

Further, in some embodiments, at least one of processing component 502, locking component 506, biometric parameter unlock component 508, sleep bypass component 510, communication component 512, and unlock component 514 may be implemented as a computer having tangible computer-readable media for carrying or having computer-executable instructions or data structures stored thereon. Such tangible computer-readable media can be any available media that can be accessed by a general purpose or special purpose computer. Non-limiting examples of tangible computer-readable media include physical storage and/or memory media such as RAM, ROM, EEPROM, CD-ROM or other optical disk storage, magnetic disk storage or other magnetic storage devices, or any other medium which can be used to carry or store desired program code means in the form of computer-executable instructions or data structures and which can be accessed by a general purpose or special purpose computer. For information transferred or provided over a network or another communications connection (either hardwired, wireless, or a combination of hardwired or wireless) to a computer, the computer may properly view the connection as a computer-readable medium. Thus, any such connection may be properly termed a computer-readable medium. Combinations of the above should also be included within the scope of computer-readable media.

Processing component 502 communicates with user interface component 504 via communication channel 520. Processing component 502 may be any type of device or system that processes commands from user interface component 504 and executes the commands. As a non-limiting example, a user may touch a portion of the user interface component 504 to indicate that the user desires to open a specific application. Processing component 502 opens the specific application as desired by the user.

User interface component 504 communicates with processing component 502 via communication channel 520, and with locking component 506 via communication channel 524. User interface component 504 may be any type of device or system that displays information to the user, and the user can manipulate the display to send commands to processing component 502. A non-limiting example of user interface component 504 is a touch screen.

Locking component 506 communicates with biometric parameter unlock component 508 via communication channel 526, and with unlock component 514 via communication channel 522. Locking component 506 may be any type of device or system that prevents a user from accessing the mobile device 100 until locking component 506 is disabled. Non-limiting examples of ways by which locking component 506 may be disabled include passcode screens or dot-patterns screens as described with reference to FIGS. 1-2.

Biometric parameter unlock component 508 communicates with locking component 506 via communication channel 526, and with sleep bypass component 510 via communication channel 528. Biometric parameter unlock component 508 may be any type of device or system that disables unlock component 506 when the proper biometric parameter is sensed. Non-limiting examples of biometric parameter unlock component 508 include fingerprint recognition, face recognition, retina recognition, and voice recognition.

Sleep bypass component 510 communicates with biometric parameter unlock component 508 via communication channel 528, and with communication component 512 via communication channel 530. Sleep bypass component 510 may be any type of device or system that disables biometric parameter unlock component 508 when sleep bypass component 510 determines that the user is sleeping or otherwise unconscious. Non-limiting examples of ways by which sleep bypass component may determine that a user is sleeping include analyzing the user's pulse, respiration, blood pressure, position, or changes thereof.

Communication component 512 communicates with sleep bypass component 510 via communication channel 530, and with communication component 516 via communication channel 532. Communication component 512 may be any type of device or system that can send and receive information. Communication component 512 receives information from communication component 516 and provides the information to sleep bypass component 510.

Unlock component 514 communicates with locking component 506 via communication channel 522. Unlock component 514 may be any type of device or system that disables locking component 506 when the proper unlock code is entered. Non-limiting examples of unlock component 514 include number passcodes and dot-pattern passcodes.

Communication component 516 communicates with communication component 512 via communication channel 532, and with detecting component 518 via communication channel 534. Communication component 516 may be any type of device or system that can send and receive information. Communication component 516 receives information from detecting component 518 and provides the information to communication component 512.

Detecting component 518 communicates with communication component 516 via communication channel 534, and with a user via communication channel 536. Detecting component 518 may be any type of device or system that can detect information about a user. Non-limiting examples of detecting component 518 include pulse sensors, respiration sensors, blood pressure sensors, gyroscopes, and accelerometers. Detecting component 518 detects a user's biometric parameters and provides information about those biometric parameters to communication component 516.

Figure 6:
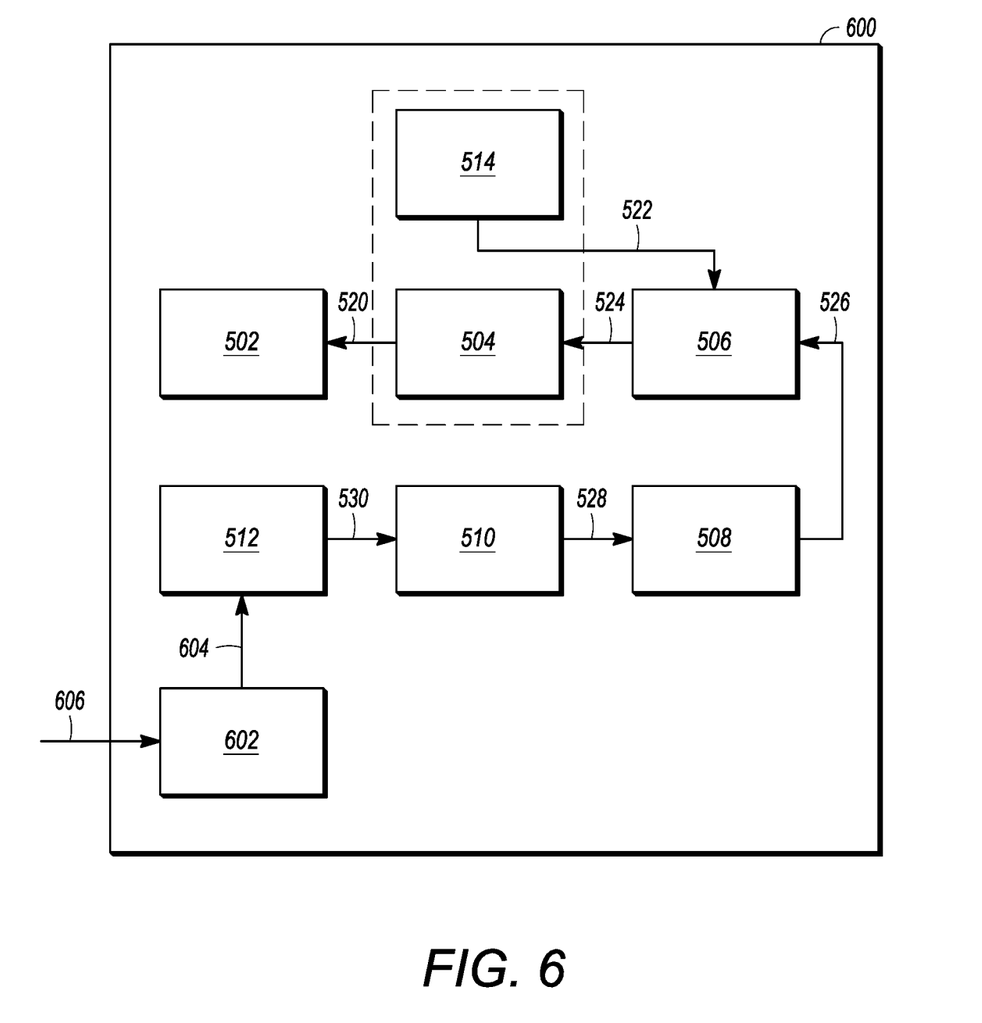
FIG. 6 illustrates a block diagram of another mobile device in accordance with aspects of the present invention.

FIG. 6 illustrates a block diagram of another mobile device in accordance with aspects of the present invention.

Mobile device 600 differs from mobile device 500 of FIG. 5, in that mobile device 600 includes a detecting component 602.

Detecting component 602 communicates with communication component 512 via communication channel 604, and with a user via communication channel 606. Detecting component 602 may be any type of device or system that can detect information about a user. Non-limiting examples of detecting component 602 include pulse sensors, respiration sensors, blood pressure sensors, gyroscopes, and accelerometers. Detecting component 602 detects a user's biometric parameters and provides information about those biometric parameters to communication component 512.

With mobile device 600, a separate wearable device is not needed to detect whether the user is sleeping. In particular, mobile device 600 detects whether the user is sleeping via detecting component 602.

Figure 7:
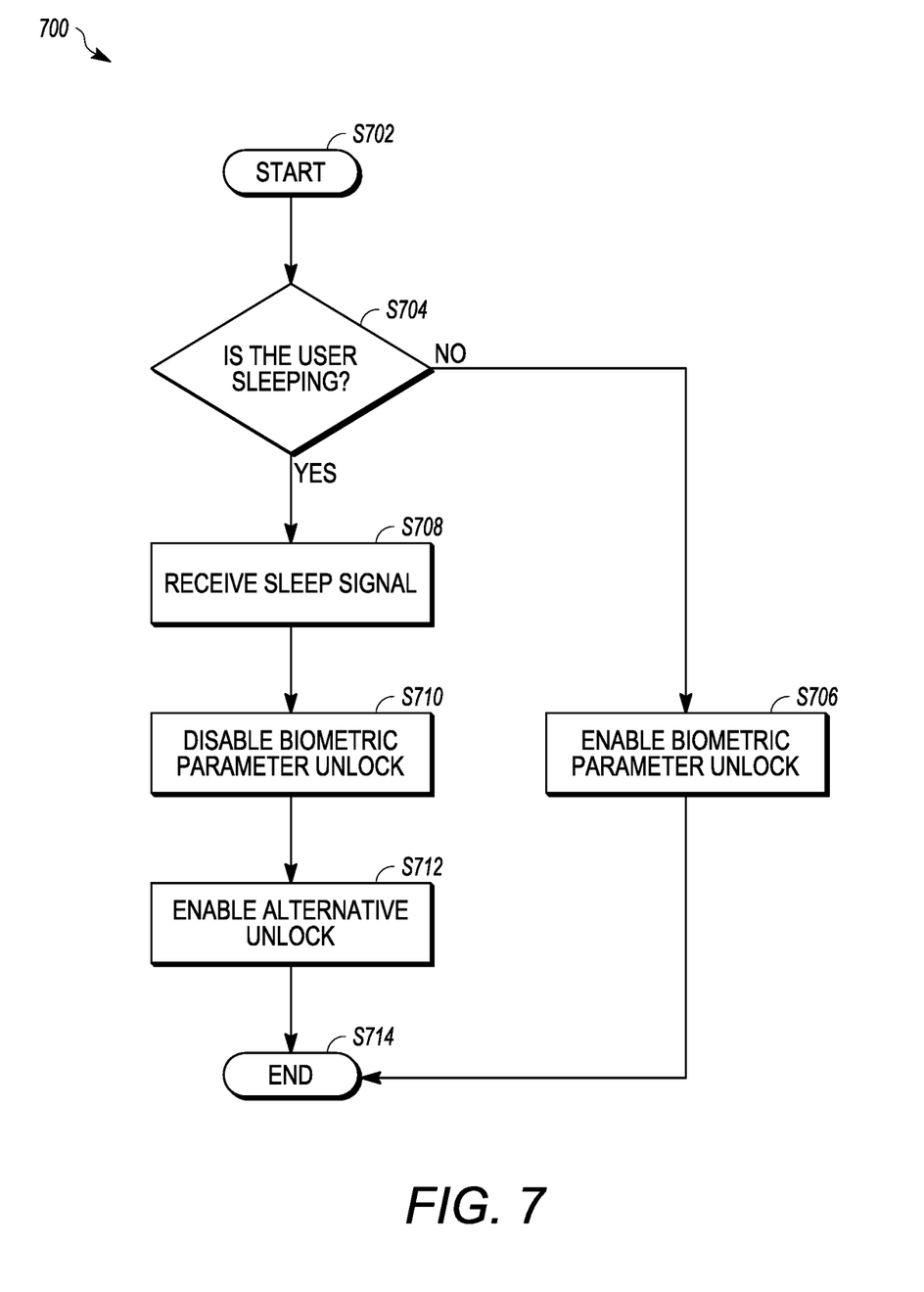
FIG. 7 illustrates a method by which biometric parameter unlocking capability is enable or disabled in accordance with aspects of the present invention.

FIG. 7 illustrates a method by which biometric parameter unlocking capability is enable or disabled in accordance with aspects of the present invention.

As shown in the figure, method 700 starts (S702) and a determination is made as to whether the user is sleeping (S704).

For purposes of explanation, consider a scenario where a user has a mobile device that includes a biometric parameter unlock that unlocks the mobile device when the mobile device recognizes his fingerprint. Further, consider a scenario where the user is exercising.

Returning to FIG. 5, wearable device 304 is in contact with the user's body during exercise. Detecting component 518 may detect the user's biometric data, non-limiting examples of which include pulse, respiration, blood pressure, position, and acceleration. Detecting component 518 then provides the data to communication component 516. Communication component 516 provides the data to mobile device 100 by sending the data to communication component 512, and communication component 512 forwards the data to sleep bypass component 510.

Sleep bypass component 510 will analyze the data and determine, via conventional means, whether the user is sleeping. In this scenario, because the user is exercising, sleep bypass component 510 determines that the user is not sleeping because the user's biometric data is consistent with that of a person who is awake.

In an alternate embodiment, and with reference to FIG. 6, the user may not use a wearable device to track his activity. Instead, the user may use mobile device 600 to track his activity. In that case, detecting component 602 may detect the user's biometric data, including, but not limited to, pulse, respiration, blood pressure, position, and acceleration. Detecting component 602 then provides the data to communication component 512, and communication component 512 forwards the data to sleep bypass component 510.

Returning to FIG. 7, after sleep bypass component 510 determines the user is not sleeping (NO at S704), the biometric parameter unlock is enabled (S706).

Referring to FIG. 5, sleep bypass component 510 notifies biometric parameter unlock component 508 that the user is awake, and biometric parameter unlock component 508 is activated. After biometric parameter unlock component 508 is activated, the user can unlock mobile device 100 using his fingerprint.

For example, suppose the user notices that he received a text message while he was working out. The user stops working out to reply to the text message. When the user looks at his phone, he sees a screen similar to that shown in FIG. 2, where he must place his finger on the screen so biometric parameter unlock component 508 can read his fingerprint. After reading his fingerprint and confirming he is the authorized user of mobile device 100, biometric parameter unlock component 508 disables locking component 506, allowing the user to interact with user interface component 504 to instruct processing component 502 to open his text messages so he can respond to the message he received.

Returning to FIG. 7, process 700 ends (S714).

Now, consider an alternate scenario in which the user completed his exercise, went to bed, and is now sleeping (YES at S704).

Referring to FIG. 7, the sleep signal is received (S708).

Returning to FIG. 5, sleep bypass component 510 detects that the user is sleeping because the user's biometric data indicates that he is asleep. For example, the user's respiration rate may be much slower than when he is typically awake, or the user's body temperature may be lower than when he is typically awake. Sleep bypass component 510 may also detect the user's position and determine that, because the user has been laying down for a certain amount of time, he is asleep. After sleep bypass component 510 determines that the user is sleeping, it generates a sleep signal and forwards the signal to biometric parameter unlock component 508.

Returning to FIG. 7, the biometric parameter unlock function is disabled (S710).

Referring to FIG. 5, biometric parameter unlock component 508 receives the sleep signal from sleep bypass component 510. The sleep signal instructs biometric parameter unlock component 508 to cease operation until the user is awake.

The user can feel secure going to sleep knowing that the data on his mobile device is secure. For example, if the user was on a train and fell asleep, a criminal may try to steal the user's information by unlocking the user's phone. If biometric parameter unlock component 508 was not disabled, the criminal could just hold the user's finger to the mobile device and successfully unlock it, and then steal the information on the mobile device. With biometric parameter unlock component 508 disabled, though, a non-approved person would be unable to successfully unlock the mobile device.

Returning to FIG. 7, an alternative unlock is enabled (S712).

Referring to FIG. 5, when biometric parameter unlock component 508 is disabled, unlock component 514 is enabled to provide an alternate way to unlock the device when a user is sleeping.

For example, suppose the user is sleeping, but is gradually waking up and wants to check his emails. Sleep bypass component 510 may not yet detect that the user is awake, so biometric parameter unlock component 508 may still be disabled. To avoid a scenario where a user must sit up or get out of bed for sleep bypass component 510 to enable biometric parameter unlock component 508 so the user can unlock the phone, unlock component 514 provides an alternate way to unlock the mobile device. The user may be able to unlock the phone using a numeric passcode or a dot-pattern passcode.

Returning to FIG. 7, method 700 ends (S714).

In summary, the present invention provides a device and method to secure a user's mobile device when the user is sleeping or otherwise unconscious. When a wearable device, or the mobile device, detects that the user is sleeping, biometric parameter unlocking mechanisms are disabled to prevent criminals from unlocking the mobile device and stealing private information. When the biometric parameter unlocking mechanisms are disabled, alternate unlocking mechanisms are enabled so the mobile device can still be unlocked by someone who knows the passcode.

The foregoing description of various preferred embodiments have been presented for purposes of illustration and description. It is not intended to be exhaustive or to limit the invention to the precise forms disclosed, and obviously many modifications and variations are possible in light of the above teaching. The example embodiments, as described above, were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed as new and desired to be protected by Letters Patent of the United States is:

1. A device for use by a user, said device comprising:
   a processing component operable to perform a processing function;
   a user interface component operable to instruct said processing component to perform the processing function;
   a locking component operable to prevent said user interface component from instructing said processing component to perform the processing function;
   an unlock component operable to control said locking component in response to receipt of an unlock code from said user interface;
   a detecting component operable to detect a biometric parameter of the user;
   a sleep bypass component operable to receive the biometric parameter of the user and generate a sleep signal based on the biometric parameter indicating the user is sleeping and to communicate the sleep signal to the biometric parameter unlock component, and
   a biometric parameter unlock component operable to receive the sleep signal, the sleep signal instructing the biometric parameter unlock component to cease operation and prevent communication with said unlock component until said biometric parameter unlock component detects the biometric parameter of the user indicating the user is not sleeping.

2. The device of claim 1, wherein said biometric parameter unlock component is operable to receive notification from the sleep bypass component that the user is awake, the biometric parameter unlock component disabling the unlocking component, detecting unlock data as one of the group consisting of a fingerprint, a retina image, a voice sample, face and combinations thereof, and providing the unlock data to the unlocking component.

3. The device of claim 2, further comprising a second unlock component operable to disable said locking component to enable said user interface component to instruct said processing component to perform the processing function.

4. The device of claim 3, wherein second unlock component comprises said user interface component, wherein said user interface component comprises a plurality of selectable keys, and wherein an unlock code is operable to be entered via said plurality of selectable keys to disable said locking component.

5. The device of claim 4, wherein said detecting component comprises a communication component operable to wirelessly receive a sleep parameter signal associated with the biometric parameter of the user.

6. The device of claim 4, wherein said detecting component comprises a parameter detector operable to detect the biometric parameter of the user.

7. The device of claim 6, wherein said parameter detector is operable to detect the biometric parameter of the user as one of the group consisting of pulse, heart rate, blood pressure, respiration, change in pulse, change in heart rate, change in blood pressure, change in respiration, and combinations thereof.

8. A method comprising:
   locking, via a locking component, a user interface component to prevent the user interface component from instructing a processing component to perform a processing function;
   unlocking, via an unlock component, said locking component in response to receipt of an unlock code from said user interface;
   detecting, via a biometric parameter unlock component, a biometric parameter of the user;
   generating, via a detecting component, biometric parameter of the user;
   generating, via a sleep bypass component, a sleep signal based on analysis of the biometric parameter indicating the user is sleeping;
   communicating the sleep signal to a biometric parameter unlock component; and
   upon receiving the sleep signal, ceasing operation of the biometric parameter unlock component and preventing communication with said unlock component until the biometric unlock component receives a biometric parameter of the user indicating the user is not sleeping.

9. The method of claim 8, further comprises receiving, via a biometric parameter unlock component, the biometric parameter of the user indicating the user is not sleeping and detecting unlock data comprising one of the group consisting of a fingerprint, a retina image, a voice sample and combinations thereof.

10. The method of claim 9, further comprising disabling, via a second unlock component, the locking component to enable the user interface component to instruct the processing component to perform the processing function.

11. The method of claim 10, wherein the second unlock component comprises the user interface component, wherein the user interface component comprises a plurality of selectable keys, and said method comprises receiving an unlock code entered via the plurality of selectable keys and disabling the locking component based on the receiving of the unlock code.

12. The method of claim 11, wherein said detecting, via a biometric parameter unlock component, a biometric parameter of the user comprises wirelessly receiving, via a communication component, a sleep parameter signal associated with the biometric parameter of the user.

13. The method of claim 11, wherein said detecting, via a biometric parameter unlock component, a biometric parameter of the user comprises detecting, via a parameter detector, the biometric parameter of the user.

14. The method of claim 13, wherein said detecting, via a parameter detector, the biometric parameter of the user comprises detecting the biometric parameter of the user as one of the group consisting of pulse, heart rate, blood pressure, respiration, change in pulse, change in heart rate, change in blood pressure, change in respiration, and combinations thereof.

15. A non-transitory, tangible, computer-readable media having computer-readable instructions stored thereon, the computer-readable instructions being executable by a computer to instruct the computer to perform a method comprising:
    locking, via a locking component, a user interface component to prevent the user interface component from instructing a processing component to perform a processing function;
    unlocking, via an unlock component, said locking component in response to receipt of an unlock code from said user interface;
    detecting, via a biometric parameter unlock component, a biometric parameter of the user;
    generating, via a detecting component, biometric parameter of the user;
    generating, via a sleep bypass component, a sleep signal based on analysis of the biometric parameter indicating the user is sleeping;
    communicating the sleep signal to a biometric parameter unlock component; and
    upon receiving the sleep signal, ceasing operation of the biometric parameter unlock component and preventing communication with said unlock component until the biometric unlock component receives a biometric parameter of the user indicating the user is not sleeping.

16. The non-transitory, tangible, computer-readable media of claim 15, wherein the computer-readable instructions are executable by the computer to instruct the computer to perform the method further comprising receiving, via a biometric parameter unlock component, the biometric parameter of the user indicating the user is not sleeping and detecting unlock data comprising one of the group consisting of a fingerprint, a retina image, a voice sample and combinations thereof.

17. The non-transitory, tangible, computer-readable media of claim 16, wherein the computer readable instructions are executable by the computer to instruct the computer to perform the method further comprising disabling, via a second unlock component, the locking component to enable the user interface component to instruct the processing component to perform the processing function.

18. The non-transitory, tangible, computer-readable media of claim 17, wherein the second unlock component comprises the user interface component, the user interface component comprises a plurality of selectable keys and the computer-readable instructions are executable by the computer to instruct the computer to receive an unlock code entered via the plurality of selectable keys and disable the locking component based on the receiving of the unlock code.

19. The non-transitory, tangible, computer-readable media of claim 18, wherein the computer-readable instructions are executable by the computer to instruct the computer to perform the method such that wherein said detecting, via a biometric parameter unlock component, a biometric parameter of the user comprises wirelessly receiving, via a communication component, a sleep parameter signal associated with the biometric parameter of the user.

20. The non-transitory, tangible, computer-readable media of claim 18, wherein the computer-readable instructions are executable by the computer to instruct the computer to perform the method such that wherein said detecting, via a biometric parameter unlock component, a biometric parameter of the user comprises detecting, via a parameter detector, the biometric parameter of the user.

* * * * *